United States Patent
Huang

(10) Patent No.: US 6,872,409 B2
(45) Date of Patent: Mar. 29, 2005

(54) COMPOSITION OF TRADITIONAL CHINESE MEDICINES FOR PREVENTING AND TREATING CEREBROVASCULAR DISEASE

(75) Inventor: Ken-Shung Huang, Taipei (TW)

(73) Assignee: BrainGenesis Biotechnology Co., Ltd., Taipei (TW)

(*) Notice: Subject to any disclaimer, the term of this patent is extended or adjusted under 35 U.S.C. 154(b) by 9 days.

(21) Appl. No.: 10/133,856

(22) Filed: Apr. 26, 2002

(65) Prior Publication Data

US 2003/0072818 A1 Apr. 17, 2003

(30) Foreign Application Priority Data

Oct. 17, 2001 (TW) ......................................... 90125718 A

(51) Int. Cl.⁷ .............................................. A61K 35/78
(52) U.S. Cl. ....................... 424/725; 775/774; 775/776; 775/777
(58) Field of Search .............................. 424/195.1, 725, 424/775, 774, 776, 777

(56) References Cited

U.S. PATENT DOCUMENTS

| 4,842,859 A | 6/1989 | Liu ......................... 424/195.1 |
| 5,589,182 A | 12/1996 | Tashiro et al. .............. 424/423 |
| 6,093,403 A * | 7/2000 | Huo et al. ............. 424/195.15 |
| 6,123,946 A | 9/2000 | Wei ......................... 424/195.1 |
| 6,365,198 B1 | 4/2002 | Niazi ......................... 424/725 |
| 6,447,814 B1 | 9/2002 | Lee et al. .................... 424/725 |

FOREIGN PATENT DOCUMENTS

| CN | 1097341 A | 1/1995 |
| IE | 78 451 A | 2/1998 |
| JP | 6-107555 | 4/1994 |
| JP | 7-324039 | 12/1995 |
| JP | 9-208479 | 8/1997 |
| WO | WO00/27224 * | 5/2000 |
| WO | WO 02/78722 A1 | 10/2002 |

\* cited by examiner

*Primary Examiner*—Patricia Leith
(74) *Attorney, Agent, or Firm*—Fish & Richardson P.C.

(57) ABSTRACT

The present invention provides a composition including at least six of the following traditional Chinese medicines: Ren Shen, Dang Gui, Huang Qi, Gan Cao, Chai Hu, Huang Lian, Tian Zhu Huang, Huang Qin. The composition possesses pharmaceutical activities of inhibiting platelet aggregation and prolonging bleeding time, and can be used in preventing and treating a cerebrovascular disease.

12 Claims, 1 Drawing Sheet

| Ren Shen | 人參 |
| Dang Gui | 當歸 |
| Huang Qi | 黃耆 |
| Gan Cao | 甘草 |
| Chai Hu | 柴胡 |
| Huang Lian | 黃連 |
| Tian Zhu Huang | 天竹黃 |
| Huang Qin | 黃芩 |

Fig. 1

COMPOSITION OF TRADITIONAL CHINESE MEDICINES FOR PREVENTING AND TREATING CEREBROVASCULAR DISEASE

FIELD OF THE INVENTION

The present invention relates to a composition of traditional Chinese medicines possessing activities of inhibiting platelet aggregation and prolonging bleeding time, which can be used to prevent and treat ischemic cerebrovascular disease (ischemic stroke).

BACKGROUND OF THE INVENTION

So far, certain Chinese medicines may claim to have pharmacological activity in inhibiting platelet aggregation or prolong bleeding time, yet no Chinese medicines are proved to possess significant pharmacological potential in preventing and treating ischemic cerebrovascular disease.

SUMMARY OF THE INVENTION

The present invention provides a novel composition of traditional Chinese medicines.

More specifically, the present invention is related to a novel composition of traditional Chinese medicines with an activity of inhibiting platelet aggregation.

Also, the present invention is related to a novel composition of traditional Chinese medicines that can prolong bleeding time.

Further, the present invention is related to a novel composition of traditional Chinese medicines that can be used in preventing and treating cerebrovascular disease, and in particular ischemic cerebrovascular disease.

Meanwhile, the present invention also discloses a use of traditional Chinese medicines in the manufacture of a medicament for preventing and treating cerebrovascular disease in a patient, and in particular ischemic cerebrovascular disease.

The novel composition of traditional Chinese medicines of the present invention comprises at least six of the followings: Ren Shen, Dang Gui, Huang Qi, Gan Cao, Chai Hu, Huang Lian, Tian Zhu Huang, Huang Qin. These traditional Chinese medicines are translated into English according to their pronunciations in Mandarin.

BRIEF DESCRIPTION OF THE DRAWING

FIG. 1 shows Chinese characters of the traditional Chinese medicines used in the present invention, and their English translations according to their pronunciations in Mandarin.

DETAILED DESCRIPTION OF THE INVENTION

The present invention provides a novel composition of traditional Chinese medicines comprising at least six, preferably seven, and more preferably all, of the followings: Ren Shen, Dang Gui, Huang Qi, Gan Cao, Chai Hu, Huang Lian, Tian Zhu Huang, Huang Qin. These traditional Chinese medicines are translated into English according to their pronunciations in Mandarin, and their Chinese characters are shown in FIG. 1. When the composition of traditional Chinese medicines of the present invention comprises six traditional Chinese medicines, Chai Hu and Huang Lian are omitted. When the composition of traditional Chinese medicines of the present invention comprises seven traditional Chinese medicines, Huang Lian is omitted.

The present invention also discloses a use of the composition of traditional Chinese medicines of the present invention in the manufacture of a medicament for preventing and treating a cerebrovascular disease, preferably an ischemic cerebrovascular disease, in a patient.

The present invention further discloses a method of preventing and treating a cerebrovascular disease, preferably an ischemic cerebrovascular disease, in a patient, which comprises administering to the patient a therapeutically-effective amount of the composition of traditional Chinese medicines of the present invention.

The composition of traditional Chinese medicines, prepared according to one of the preferred embodiments of the present invention, was demonstrated to possess pharmaceutical activities of inhibiting platelet aggregation and prolonging bleeding time. The same composition of traditional Chinese medicines was also proven to possess therapeutic effect on preventing and treating an ischemic cerebrovascular disease through animal experiments, and shown having no safety concern through safety pharmaceutical tests and subacute toxicology tests (28 days).

Preferably, the eight traditional Chinese medicines are in the form of dry powder. The eight traditional Chinese medicines can be obtained from the general traditional Chinese medicine store, which are processed separately, baked to dry and grinded into powder.

According to the present invention, the ratio (by weight) of the eight traditional Chinese medicines is, preferably, Ren Shen: Dang Gui: Huang Qi: Gan Cao: Chai Hu: Huang Lian: Tian Zhu Huang: Huang Qin=140±10%: 166±10%: 180±10%: 67±10%: 140±10%: 120±10%: 120±10%: 67±10%. The amount of the one or two unused traditional Chinese medicines are zero, while the weight ratio of the others remaining unchanged, in the case when the composition of the present invention comprises six or seven traditional Chinese medicines out of the eight traditional Chinese medicines.

The composition of traditional Chinese medicines of the present invention is suitable to be administered orally.

Ren Shen (*Ginseng* radix) used in the present invention includes (but not limited to) *Panax ginseng* C.A. Meyer and *Panax quinquefolium* Linnaeus, and the former is preferred. Ren Shen acquired from the traditional Chinese medicine stores or trading companies is processed by steaming Ren Shen in a meshed steamer with a mixture of pure water and rice wine (3:1), which is quickly boiled with a strong fire and then with a mild flame for 90 minutes; drying and slicing the steamed Ren Shen after cooling down. Then, the Ren Shen ginseng slices are placed in an oven, and baked at 50° C. for 13 hours, and grinded into powder. One thousand grams of Ren Shen (*Panax ginseng* C.A. Meyer) become approximately 930 grams after the processing.

Dang Gui (*Angelica sinensis* radix) used in the present invention includes (but not limited to) the root of *Angelica sinensis* (Oliv.) Diels. The unsliced Dang Gui, acquired from the traditional Chinese medicine stores or trading companies, is processed by quickly washing it with water spray until the waste water becomes clear, and then washing with distilled water. The clean Dang Gui (20 kg) is steamed in a meshed steamer by boiling a mixture of 3 kg of R.O. water, 1 kg of rice wine, and 100 gm of Cyperi Rhizoma (*Cyperus rotundus* L.), which is quickly boiled with a strong fire and then with a mild flame for 60 minutes, and sliced after cooling down. The Dang Gui slices are placed in an automated oven, baked for 10 hours at 55° C., and grinded into powder. One thousand grams of Dang Gui become approximately 600 grams after being processed to dry powder. According to U.S. Pat. No. 4,843,067, both *Levisticum officinale* Koch and *Angelica archangelica* can be contemplated as a substitute of Dang Gui.

Huang Qi (*Astragali* radix) used in the present invention includes (but not limited to) the roots of *Astragalus membranaceus* (Fisch.) *Bunge* var. membranaceus, *Astragalus membranaceus* (Fisch.) *Bunge* var. mongholicus (*Bunge*) Hsiao, and *Hedysarum polybotrys* Hand.-Mazz. Huang Qi, acquired from traditional Chinese medicine stores or trading companies, is processed, which comprises washing Huang Qi with water, slicing, drying it by baking it in an oven at 50° C. for 16 hours, and grinding the dried slices into powder. One thousand grams of Huang Qi become approximately 650 grams after the processing.

Gan Cao used in the present invention is the rhizome of *Glycyrrhiza uralensis* Fisch., *Glycyrrhiza glabra* L. or *Glycyrrhiza inflata* Bat. and preferably *Glycyrrhiza uralensis* Fisch. Gan Cao, acquired from traditional Chinese medicine stores or suppliers, is processed by water-washing, slicing, baking at 50° C. for 12 hours, and grinding into powder. One thousand grams of Gan Cao become approximately 720 grams after the processing.

Chai Hu (*Bupleurum* radix) used in the present invention is the roots of *Bupleurm chinensis* DC, *Bupleurum scorzonerifolium* Willd., and other plants in the same genus, and preferably is the root of *Bupleurm chinensis* DC. Chai Hu, acquired from traditional Chinese medicine stores or suppliers, is processed by water-washing, drying by baking for 12 hours, and grinding into powder. One thousand grams of Chai Hu become approximately 720 grams after the processing.

Huang Lian used in the present invention is rhizome of *Coptis chinensis* Franch., *Coptis deltoidea* C.Y. Cheng et Hsiao, *Coptis teetoides* C.Y. Cheng, and other plants in the same genus. Huang Lian, acquired from traditional Chinese medicine stores or suppliers, is processed by water-washing, baking at 50° C. for 12 hours, and grinding into powder. One thousand grams of Huang Lian become approximately 750 grams after the processing.

Tian Zhu Huang (*Bambusae concretio* silicea) used in the present invention is a bulk accumulated between nodes of a stem of *Phylllostachys nigra* MUNRO var. henonis STAPF ex RENDLE) and other plants in the same genus. Tian Zhu Huang, acquired from traditional Chinese medicine stores or suppliers, is screened by choosing those floating on water, which is baked at 55° C. for 18 hours, and grinded into powder. One thousand grams of Tian Zhu Huang become approximately 850 grams after the processing.

Huang Qin (*Scutellariae* radix) used in the present invention is the root of *Scutellaria baicalensis* Georgi. Huang Qin, acquired from traditional Chinese medicine stores or suppliers, is processed by washing it with water. The clean Huang Qin (10 kg) is steamed in a meshed steamer by boiling a mixture of 3 kg of R.O. water and 100 gm of *Corni Fructus,* which is quickly boiled with a strong fire and then with a mild flame for 60 minutes, and sliced after cooling down. The Huang Qin slices are placed in an automated oven, baked for 11 hours at 50° C., and grinded into powder. One thousand grams of Huang Qin become approximately 700 grams after the processing.

PREPARATION EXAMPLE

*Panax ginseng,* Dang Gui, Huang Qi, Gan Cao, Chai Hu, Huang Lian, Tian Zhu Huang, Huang Qin were purchased from traditional Chinese medicine suppliers. Based on the source identification, *Panax ginseng* belonged to *Panax ginseng* C.A. Meyer, Dang Gui belonged to *Angelica sinensis* (Oliv.) Diels, Huang Qi belonged to *Hedysarum polybotrys* Hand.-Mazz., Gan Cao belonged to *Glycyrrhiza uralensis* Fisch., Chai Hu belonged to *Bupleurum longesadiatum* Turca., Huang Lian belonged to *Coptis chinensis* Franch., Tian Zhu Huang was from *Bambusa textilis* McCluture; *Schizostachyum chinense* Rendle, and Huang Qin belonged to *Scutellaria baicalensis* Georgi. These eight traditional Chinese medicines were processed according to the processing steps described above, the resulting dry powders were sieved with a mesh No. 10 sieve, and the penetrated portions were used.

The eight traditional Chinese medicines in the powder form were mixed according to the following weight ratio: *Panax ginseng:* Dang Gui: Huang Qi: Gan Cao: Chai Hu: Huang Lian: Tian Zhu Huang: Huang Qin=140: 166: 180: 67: 140: 120: 120: 67, and a powder pharmaceutical composition was obtained, which is named as BNG-1.

Example 1

1. Test substance and Dosing pattern

BNG-1 was provided by BrainGenesis Biotechnology Co., Ltd., Taiwan, and dissolved in distilled water. For oral administration (PO) in in vivo testing, the dosage is 20 ml/kg for mice. Tested animals received an initial dosage of 1000 mg/kg daily for 8 consecutive days. For in vitro assays, 0.1 ml of testing material was added to the 10 ml bath to give a final concentration of 1000 $\mu$g/ml, and incubated with isolated tissues for 5 minutes before evaluation of possible agonist response or challenge with agonists in the Arachidonic Acid Platelet Aggregation.

2. Animals

In these studies, male/female ICR derived mice, and New Zealand derived albino male/female rabbits provided by animal breeding center of MDS Panlabs Taiwan, Ltd. were used. All animals were maintained in a controlled temperature (22° C.–24° C.) and humidity (60%–80%) environment with 12 hours light dark cycles for at least one week in MDS Panlabs Taiwan laboratory prior to be used.

3. Method

Arachidonic Acid, Platelet Aggregation Agonism/Antagonism

Venous blood obtained from male or female New Zealand derived albino rabbits weighing 2.5–3 kg was used. Blood sample was mixed with one-tenth volume of trisodium citrate (0.13M) and centrifuged at room temperature for 10 min at 220 g. Testing substance by volume of 0.025 ml was added to the 0.45 ml tissue bath to get a testing concentration of 1000 $\mu$g/mL. The aggregation of the platelet enriched plasma ($6\times10^8$ platelets/ml) by 50 percent or more ($\geq 50\%$) within 5 minutes, relative to 100 $\mu$M Arachidonic acid control response at 37° C. as measured by an optical aggregometer, indicated possible Arachidonic acid receptor agonist activity. At a test substance concentration where no significant agonist activity was seen, the ability to reduce the Arachidonic acid-induced maximum non-reversible aggregation response by –50 percent or more ($\geq 50\%$) indicated Arachidonic acid receptor antagonist activity. Each concentration was tested two separate preparations.

The concentration of 50% inhibition of aggregation induced by 100 $\mu$M Arachidonic acid ($IC_{50}$) of BNG-1 was also determined, which is 176.5 $\mu$g/ml.

Bleeding Time (PO)

A group of 5 ICR derived male mice weighing 22±2 g was administered PO at the dosage of 1000 mg/kg daily for seven days and one dosage of 1000 mg/kg was administered orally one hour before standardized transection of the tip (0.5 mm) of each tail on the eighth day. The mice, in holders, were immediately suspended vertically with the distal 2 cm of each tail immersed in a test tube containing saline at 37° C. The time required for bleeding to cease over a period of 15 seconds was then determined. A maximun cut-off time of 180 seconds was set. Prolongation of bleeding time by 50 percent or more ($\geqq 50\%$) relative to a control group of animals was considered significant.

4. Results:

| AA-platelet Agg - in vitro antag | | 1000 μ/ml | 100% | n = 2 |
|---|---|---|---|---|
| AA-platelet Agg - in vitro antag | | 300 μg/ml | 100% | n = 2 |
| AA-platelet Agg - in vitro antag | | 100 μg/ml | 0% | n = 2 |
| Bleeding time | PO | 1000 mg/kg × 8 | 60% | n = 5 |
| Bleeding time | PO | 1000 mg/kg × 8 | 63% | repeat n = 5 |
| Bleeding time | PO | 300 mg/kg × 8 | 0% | n = 5 |

Control Example 1

BNG-4, BNG-5, BNG-6 and BNG-7 were prepared similarly as BNG-1 in Preparation Example, except that some of the eight Chinese herb medicines of BNG-1 were omitted while the weight proportions remaining the same.

The procedures of Arachidonic Acid, Platelet Aggregation Agonism/Antagonism test method in Example 1 were repeated to determine $IC_{50}$ of BNG-4, BNG-5, BNG-6 and BNG-7. The formulas and results of BNG-4, BNG-5, BNG-6 and BNG-7 are shown as follows in comparison with $IC_{50}$ of BNG-1.

| Test substance | $IC_{50}$ (concentration of 50% inhibition of aggregation induced by 100 μM Arachidonic acid) |
|---|---|
| BNG-1 | 176.5 μg/ml |
| BNG-4 (Dang Gui and Huang Qi omitted) | 406.6 μg/ml |
| BNG-5 (Dang Gui and Chai Hu omitted) | 379.2 μg/ml |
| BNG-6 (Huang Qin and Huang Lian omitted) | 393.7 μg/ml |
| BNG-7 (Dang Gui, Chai Hu, Huang Qin and Huang Lian omitted) | >1000 μg/ml |

Example 2

1. Test Substances and Dosing Pattern

Group 1 (5 rats): Vehicle Control

Saline was given orally (PO) in a dosage of 10 mL/kg immediately after MCAO and day 1, then every 24 hours for 7 consecutive days totally.

Group 2 (5 rats): Positive Control (MK-801)

MK-801 was given by intraperitoneally (IP) injection at a dose of 0.3 mg/kg in a dosage of 5 mL/kg at 0, 6, 24, 30, 48 and 54 hours after MCAO.

Group 3 (5 rats): BNG-1 treatment

BNG-1 dissolved in saline was given orally (PO) at a dosage of 1000 mg/kg in a dosing volume of 10 mL/kg immediately after MCAO on day 1, then every 24 hours for 7 consecutive days in total.

2. Animals

Male Sprauge Dawely rats weighting 180–240 g (10 weeks of age) from the Animal Resources Center, Medical College of National Taiwan University were used. The animals were maintained in a controlled temperature (22° C.–24° C.) and humidity (60%–80%) environment with 12 hour light dark cycles (6:00 a.m./6:00 p.m.) for at least one week in MDS Panlabs Taiwan, Ltd laboratory prior to use.

3. Equipment

Dental drill (UPOWER UG 33, SELECTOR-M), Image Analyzer (Life Science Resources VISTA Version 3.0), Infant Incubator (Brighten Life BL-90-SC), Magnifying stereomicroscope (ZEISS, Stemi 1000), Microscissors (A. Heiss), Microtome (SHANDON, Varistain 24-4 Automatic Slide, U.K.) and Rectal thermistor probe (Harvard Homeothermic Blanket Control Unit) were used.

4. METHODS

Brain Ischemia, Middle Cerebral Artery Occlusion (MCAO)

Permanent brain ischemia via middle cerebral artery occlusion (MCAO) was carried out under chloral hydrate (500 mg/10 mL/kg IP) anesthetized. The temporoparietal region was shaved and a skin incision was made between the lateral aspect of the orbit and the external acoustic meatus. The superior pole of the parotid gland was reflected downwards as was the temporalis muscle after partial resection of its cranial insertion. The distal course of the middle cerebral artery was then visible through the translucent skull.

Under a 10× magnifying stereomicroscope, craniectomy was performed with a dental drill and then enlarged with fine synovectomy rongeurs. The middle cerebral artery at the proximal site of branch originated from interior carotid artery was cut with a microscissors after which the temporalis muscle and parotid gland were replaced. The incision was lightly dusted with kanamycin, the scalp was sutured and a 10% povidone iodine solution was topically applied. During surgery, the animals were maintained normothermic by means of a homeothermic heating system coupled to a rectal thermistor probe. Under these conditions, rectal temperature was maintained within physiological limits (37.5±1.0° C.). After surgery, animals were kept in infant incubator (37.5±1.0° C.) while recovering from anesthesia for 1 hour. After recovery, the rats were housed 5 per cage with free access to food and water and kept in a clean animal room (23.0±10° C.).

BNG-1, dissolved in saline as vehicle, was administered at doses of 1000 mg/kg (n=5) orally (PO) in a dosing volume of 10 ml/kg daily for 7 consecutively days started immediately after MCAO. The vehicle-control group (n=5) was similarly treated with saline alone. The positive control reference agent MK-801 (RBI, Natick, Mass. 01760-2447, U.S.) dissolved with saline was injected at a dose of 0.3 mg/kg intraperitoneally (IP) in a dosing volume of 5 ml/kg at 0, 6, 24, 30, 48 and 54 hours after MCAO.

On the eighth day after the ischemic insult, all animals were sacrificed by decapitation. Their brains were rapidly removed and immediately frozen at −70° C. in deep freezer (NUAIR™, NU-6511). Twenty-four hours later, whole brain coronal sections (30 μm) were obtained by use of a microtome ("SHANDON" Varistain 24-4 Automatic Slide). Every $13^{th}$ section (i.e. 390 μm apart) totally covering the infarction area of 12 mm length was selected for histological examination. Altogether 30 slices, stained by 2% cresyl violet, were used to measure the area of ischemic damage. This was quantitatively assessed by an Image Analyzer. The total ischemic area ($mm^2$) of each coronal slice from each animal was summated and expressed as the mean±SEM. The calculated infarcted volume ($mm^3$) of $mm^2 \times$specific distance (390 μm) was then expressed as the mean±SEM for each experiment group. The effect of BNG-1 and MK-801 treatment was calculated for comparison with the vehicle control group by means of the unpaired Student's t test, differences were considered significant at *P<0.05. For each animal, body temperature was recorded before 0 minutes (pre-dosage) and 30 minutes (post-dosage) after each oral administration. Tukey multiple comparison test was applied for comparison between pre-dosage and post-dosage temperatures.

5. Results

BNG-1, evaluated at a dose of 1000 mg/kg PO for 7 consecutive days post-treatment, significantly reduced (46.29%) brain ischemia in rats subjected to unilateral and permanent middle cerebral artery occlusion. No toxicity or mortality was observed in tested animals during the 7 consecutive days study. No significant change in body temperature was observed. MK-801 significantly reduced (48.38%) brain ischemia.

Example 3

Permanent brain ischemia via middle cerebral artery occlusion (MCAO) was carried out to Male Sprange Dawely rats by the same procedures as in Example 2.

BNG-1, dissolved saline as vehicle, was administered at doses of 1000 mg/kg and 500 mg/kg orally (PO) for 7 days daily before and for 3 days daily after MCAO. The vehicle-control group was similarly treated with saline alone. The positive control reference agent MK-801 was injected intraperitoneally (IP) at a dose of 0.3 mg/5 ml/kg immediately after MCAO 0, and again after 6, 24, 30, 48 and 54 hrs. On the fourth day the ischemic insult, all animals were sacrificed by decapitaiton. The total ischemic area of their brains were determined according to the same procedures as in Example 2.

Under the experimental conditions used, MCAO caused a reproducible ischemia of around 50%–60% of the affected hemisphere. For the most part, the area of damage was largely confined to various cortical regions (i.e. frontal, sensorimotor, auditory and occipital cortices) and only rarely involved damage to components of the basal ganglia. Relative to the vehicle-treated control group, MK-801 significantly reduced the total infarcted volume by $66.30 \pm 10.50\%$ at a dose of 0.3 mg/kg IP×6. At the 1000 mg/kg PO ×10 dose level, BNG-1 significantly reduced the total infarcted volume of $44.09 \pm 9.01\%$ while a non-significant $14.17 \pm 19.43\%$ reduction was observed after the 500 mg/kg×10. None of the compounds caused any significant change in body temperature.

The SAFETY PHARMACOLOGY of BNG-1 was evaluated according to the SAFETY PHARMACOLOGY testing package (non-GLP) undertaken at MDS Panlabs Taiwan, Ltd., Taiwan.

SAFETY PHARMACOLOGY test results

| Experiments | Administration route | Dosage or concentration | Activity |
|---|---|---|---|
| Mice behavior reaction-Irwin observation screening (General behavioral, autonomic, neurological sign, etc, 38 tests and 7 days toxicity lethal rate observation) | oral | 0.5, 1.0 and 2.0 (gm/kg) | No effect |
| Central nervous system (spontaneous activity motor in coordination, prolongation of hexobarbital sleeping time, protection against maximal-electroshock or pentylenetetrazole-induced convulsions and mortality, proconvulsant or anticonvulsant response and analgesic activity (tail flick response and phenylquinone-induced writhing) in mice and body temperature in rats) | oral | 0.5, 1.0 and 2.0 (gm/kg) | No effect |
| Respiration-circulation system (Alteration of mean, systolic and diastolic blood pressure, femoral blood flow, heart rate, QT interval, PR interval, QRS duration and S–T segment and respiratory rate in dogs) | oral | 1 (gm/kg) | No effect |
| Urine volume output, electrolyte excretion and urinary pH values in rats | oral | 1 (gm/kg) | No effect |
| Gastrointestinal system (Gastrointestinal Motility in mice) | oral | 1 (gm/kg) | No effect |
| Contractile responses of guinea pig ileum induced by Acetylcholine, Histamine, and Barium Chloride | In vitro | 1 (mg/ml) | Reduced contractile |
| Contractile responses of guinea pig ileum induced by Acetylcholine | In vitro | 0.3 (mg/ml) | Reduced contractile |

The result suggests that it should not have safety concern when orally applying 1 gm/kg of BNG-1 to rats.

The acute toxicity test of BNG-1

Singe dosage of BNG-1 viscous suspension (5gm/kg) was orally apply to 6 male and 6 female rats, control groups were applied with control solution without test material(1% CMC solution), and the acute toxicity of BNG-1 to rats was determined. Each rat was administered with twice (2 hours interval) of BNG-1 or control solution, undergo clinical observation for 14 days. None of them show any clinical toxicity symptom, and no symptom was observed either in organs or tissues by bare eyes after dissecting the rats. Hence, with 5 gm/kg dosage of BNG-1, it did not cause any observable acute toxicity in rats. Therefore, 5 gm/kg is the "no observable effect level" (NOEL) for BNG-1, and can be classified as practically nontoxic material.

To summarize the test results obtained in the above, it suggests that BNG-1, in 1 gm/kg, can prevent and treat ischemic cerebrovascular disease in mice; and in that dosage, it should not has any safety concern, and it does not show acute toxicity. These results evidence that BNG-1 has a great potential of preventing and treating ischemic cerebrovascular disease in human.

It also has been found that, under in vitro administration with 1 mg/ml of BNG-1, 67% relaxation activity against the spontaneous tension of respiratory tract in guinea pig ileum was observed, and 31% enhancement in contraction force of myocardium of guinea pig ileum was also observed.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A pharmaceutical composition for inhibiting platelet aggregation comprising an effective amount of the following eight medicines, Ren Shen, Dang Gui, Huang Qi, Gan Cao, Chai Hu, Huang Lian, Tian Zhu Huang, and Huang Qin as active ingredients.

2. The pharmaceutical composition according to claim 1, wherein said eight medicines are in the form of dry powder.

3. The pharmaceutical composition according to claim 2, wherein said eight medicines are in a weight ratio of Ren Shen Dang Gui Huang Qi: Gan Cao Chai Hu: Huang Lian: Tian Zhu Huang Huang Qin=140±10%: 166±10%: 180±10%: 67±10%: 140±10%: 120±10%: 120±10%: 67±10%.

4. The pharmaceutical composition according to claim 3, which is administered orally.

5. A pharmaceutical composition for prolonging bleeding time in a patient comprising an effective amount of the following eight medicines, Ren Shen, Dang Gui, Huang Qi, Gan Gao, Chai Hu, Huang Lian, Tian Zhu Huang, and Huang Qin, as active ingredients.

6. The pharmaceutical composition according to claim 5, wherein said eight medicines are in the form of dry powder.

7. The pharmaceutical composition according to claim 6, wherein said eight medicines are in a weight ratio of Ren Shen: Dang Gui Huang Qi: Gan Gao: Chai Hu: Huang Lian: Tian Zhu Huang: Huang Qin=140±10%: 166±10%: 180±10%: 67±10%: 140±10%: 120±10%: 120±10%: 67±10%.

8. The pharmaceutical composition according to claim 7, which is administered orally.

9. A pharmaceutical composition for treating an ischemic cerebrovascular disease in a patient comprising an effective amount of the following eight medicines, Ren Shen, Dang Gui, Huang Qi, Gan Cao, Chai Hu, Huang Lian, Tian Zhu Huang, and Huang Qin, as active ingredients.

10. The pharmaceutical composition according to claim 9, wherein said medicines are in the form of dry powder.

11. The pharmaceutical composition according to claim 10, wherein said eight medicines are in a weight ratio of Ren Shen: Dang Gui: Huang Qi: Gan Gao: Chai Hu: Huang Lian: Tian Zhu Huang: Huang Qin=140±10%: 166±10%: 180±10%: 67±10%: 140±10%: 120±10%: 120±10%: 67±10%.

12. The pharmaceutical composition according to claim 11, which is administered orally.

* * * * *